(12) United States Patent
Bauman et al.

(10) Patent No.: US 7,306,770 B2
(45) Date of Patent: Dec. 11, 2007

(54) HIGH TEMPERATURE COMBUSTION TUBE

(75) Inventors: Noel C. Bauman, College Station, TX (US); Gary Erickson, College Station, TX (US); Richard K. Simon, Jr., College Station, TX (US)

(73) Assignee: O.I. Corporation, College Station, TX (US)

( * ) Notice: Subject to any disclaimer, the term of this patent is extended or adjusted under 35 U.S.C. 154(b) by 154 days.

(21) Appl. No.: 10/941,761

(22) Filed: Sep. 15, 2004

(65) Prior Publication Data

US 2006/0053874 A1    Mar. 16, 2006

(51) Int. Cl.
*B01J 10/00* (2006.01)
*G01N 31/10* (2006.01)
*B01D 50/00* (2006.01)
*G01N 21/72* (2006.01)
*B32B 5/02* (2006.01)

(52) U.S. Cl. .................... 422/129; 436/34; 436/37; 436/155; 422/78; 422/170

(58) Field of Classification Search ............... 422/193; 436/37
See application file for complete search history.

(56) References Cited

U.S. PATENT DOCUMENTS

| | | |
|---|---|---|
| 4,619,902 A | 10/1986 | Bernard |
| 5,241,131 A | 8/1993 | Bakhru et al. |
| 5,250,093 A | 10/1993 | Jiang et al. |
| 5,261,937 A | 11/1993 | Jiang et al. |
| 5,358,557 A | 10/1994 | Jiang et al. |
| 5,436,165 A * | 7/1995 | Brenner .................. 436/149 |
| 5,470,380 A | 11/1995 | Jiang et al. |
| 5,528,039 A | 6/1996 | Bernard |
| 5,582,633 A | 12/1996 | Jiang et al. |
| 5,814,128 A | 9/1998 | Jiang et al. |
| 6,342,185 B1 * | 1/2002 | Dahl et al. ............... 422/82.12 |
| 6,368,865 B1 * | 4/2002 | Dahl et al. ................ 436/37 |
| 6,627,445 B1 * | 9/2003 | Akporiaye et al. ......... 436/37 |
| 6,989,131 B2 * | 1/2006 | Karlsson et al. ............ 422/99 |

FOREIGN PATENT DOCUMENTS

EP    247384 A2 * 12/1987

OTHER PUBLICATIONS

Corrella et al., Variation with Time of the Mechanism, Observable Order, and Activation Energy of the Catalyst Deactivation by Coke in the FCC Process, Industrial & Engineering Chemistry Process Design and Development 1985, 25, 625-636.*
WWW.BRAINYENCYCLOPEDIA.COM, Chromatography Definition, Misc. Info. Date and Author Unknown.
U.S. Environmental Protection Agency, Field Analytic Technologies Encyclopedia, Gas Chromatography Misc. Info. Date and Author Unknown.

* cited by examiner

*Primary Examiner*—Jill Warden
*Assistant Examiner*—Neil Turk
(74) *Attorney, Agent, or Firm*—Tod T. Tumey

(57) ABSTRACT

An improved reaction tube having an interior configured for bifurcated chambers. The present device has an inert chamber and a catalyst chamber where the materials contained therein are decoupled from one another. This improved tube is especially beneficial as it provides for greater working efficiency, preservation of catalytic materials, straightforward maintenance and replacement procedures, and effective isolation of unwanted particles.

3 Claims, 4 Drawing Sheets

HIGH TEMPERATURE COMBUSTION TUBE

BACKGROUND OF THE INVENTION

1. Field of the Invention

The present invention generally relates to an improved high temperature combustion tube generally used within a Total Organic Carbon Analyzer. More specifically, the present invention provides for a combustion tube with distinct inert and catalytic chambers; as such, inert (energy-absorbing) materials are decoupled from catalytic materials.

2. Background Information

Conventionally, the oxidative furnaces utilized in high temperature carbon-oxidative combustion contains an inner assembly tube that is fabricated from quartz. This tube is in turn packed with various layers of materials that provide a profile to ensure combustion of the carbon within the furnace.

Typical packing of the tube starts furthest from the inlet region of the tube, where the tube is loaded with catalytically active materials (such as platinum on an alumina, zirconia, or titania substrate, or platinum as a solid pellet, or platinum as a porous pellet). Above the catalytically active materials, rests an inert section of quartz wool, upon which quartz chips or quartz beads are loaded.

A sample is introduced in the top via a small injection needle. Upon impact of the sample on the top layer of either the quartz or catalyst, the sample is vaporized, generating a significant expansion pulse or shock front. The energy of the expansion pulse is transferred in both the gas phase as well as by direct solid-to-solid contact between the quartz chips or beads to the very bottom of the reactor tube. This mode of energy transfer results in chipping or flaking of the platinum catalyst, decreasing the activity and subsequent efficiency of the platinum to convert the carbon in the sample to carbon dioxide. Moreover, the fine platinum, quartz, and platinum support particles that flake off are transferred by gravity and transport gas flow, out of the active (hot) reactive zone, down to the exit vent of the reaction tube. The vent section of the reactor tube is typically at temperatures below 200 C to allow conventional coupling of the reactor tube to Teflon or other inert tubing for transport to the bulk water condenser element and/or other high-efficiency drying element.

The purported reason for the upper quartz layer (either as quartz wool, or as quartz chips, or beads) is to absorb the shock of vaporization of water contained in the sample transferred for combustion to the reaction tube. However, since the quartz chips/beads are in direct (or after multiple injections come to be in direct) contact with the catalyst, the shock of expansion is directly coupled to the platinum catalyst. The resulting impact causes the catalyst to crack and flake off of the ceramic substrate. The platinum that flakes off, or the beads that have cracks or chips typically have reduced catalytic activity. Moreover, these catalyst particles (microscopic flakes of platinum) migrate to the bottom of the furnace tube. Since this region of the furnace tube is generally of reduced temperature, the "free" catalyst particles loose their effectiveness. These free catalyst particles inadvertently increase the back pressure of the system due to blockage of the exit vent.

Another effect that occurs upon addition of sample into the reactor tube is the deposit and transport of salts and other inorganic oxides onto the initial quartz body. With time, these salts migrate or are "channeled" by various means into the catalytic body immediately below the upper quartz or other ceramic elements in the upper packing layer. These salts or inorganic oxides coat the catalyst, severely limiting the catalyst from oxidizing the organic species present in the gaseous stream. As a function of time, these salts tend to increase the back pressure, and contribute to additional coupling of shock wave energy by direct contact with the platinum substrate (i.e. the inorganic salts and oxides further accelerate the deterioration of the platinum catalyst).

Finally, instruments known in the art require the user to make and break connections to the combustion tube from both the top and bottom of that tube. This makes servicing the instrument a very difficult procedure.

In view of the limitations of combustion tubes known in the art, a great need exists for improvement with respect to these tubes. Applicant's invention provides novel solutions to the problems mentioned above. By employment of a unique interior tube configuration, Applicant's invention provides a means to decouple the shock wave propagated by direct contact between the top-layer quartz (or other energy absorbing media) and the catalytic surface. Resulting advantages of the present invention include: (1) decreased rate of deterioration of the catalytic bed, (2) uniform thermal geometry in the base of the furnace and elimination of cold regions within the catalyst bed, (3) non transport of inorganic salts and inorganic oxides onto the surface of the catalyst, (4) easier servicing of the reactor tube, and (5) reduction in the amount of catalyst required.

Applicant's invention provides for uniform thermal geometry in the base of the tube. That is, the upper section of the tube is 'cold' and the bottom surface of the tube is maintained at the same temperature as the main body of the surrounding furnace. This ensures that moisture present in the system does not condense in the combustor tube after it enters the system. Consequently, there is no regeneration of a second shock wave as the superheated gas moves from the inlet (gas expansion side) into the outlet (catalytic reaction) side of the reactor tube. Moreover, because the gas is not allowed to cool, cold regions in the catalytic volume are not established. This greatly increases the efficiency of the reaction process. Summarily, in view of the prior art, the bifurcated-chamber design of the present invention permits less catalyst to be used—primarily because uniform thermal gradients maintain efficient reaction rates, and eliminate direct coupling of the expansion shock wave energy.

While incorporation of a bifurcated-chamber design may appear to be a subtle distinction at first glance, its effects completely change the operation and maintenance of these tubes and their overall combustion systems. For instance, prior art designs require excess loading of catalyst to account for decreased efficiency and catalyst degradation. However, the present invention eliminates the requirement to load the combustion tube with an excessive amount of catalyst.

The present system prevents degraded or dislodged inert particles, and inorganic salts and oxides deposited on the inert quartz body, from being transported to the catalyst side of the reactor tube. Rather, such particles are trapped along the bottom surface of the tube. As such, these unwanted particles cannot obstruct gas flow or attach to the catalyst materials. Again, as the catalyst remains free from interfering matter, its working efficiency is preserved.

The present invention allows complete service of the combustion tube from only the top-side, making replacement or service of the combustion tube more "user" friendly. Since the platinum catalyst does not rapidly degrade, servicing of the combustion tube allows the user to reuse the platinum catalyst. This feature alone results in a substantial reduction in the cost of servicing the combustion system.

Finally, the present invention eliminates the requirement of humidification of the oxidant. In prior art designs, the catalyst limits the sorption of carbon dioxide (or degradation products containing carbon). The sorption is due to the degradation of the catalyst—caused by exposure to inorganic salts and/or oxides and the resulting "barrier" coating of the catalyst, exposure of chemically active sites, or crevices and fissures within the support phase of the catalyst. In the prior art, humidification of the catalyst serves to hydrate the inorganic salts and/or oxides, converting them into a form in which the carbon dioxide or degradation products of the oxidation process are not as strongly sorbed. As such, devices in the prior art are much more complex with regard to plumbing and servicing, as humidification reservoirs are required. Applicant's invention, however, presents a very straightforward plumbing mechanism and eliminates the need for a humidification reservoirs.

SUMMARY OF THE INVENTION

In view of the foregoing, it is an object of the present invention to provide an improved combustion tube where inert materials are decoupled from catalyst materials.

It is another object of the present invention to provide an improved combustion tube where degraded inert particles do not interfere with, or coat catalytic material.

It is another object of the present invention to provide an improved combustion tube where catalytic material is preserved throughout the combustion/oxidation process.

It is another object of the present invention to provide an improved combustion tube where catalytic material is held at a constant temperature throughout the combustion/oxidation process.

It is another object of the present invention to provide an improved combustion tube that eliminates the need for catalytic material humidification.

It is another object of the present invention to provide an improved combustion tube that is easily cleaned.

It is another object of the present invention to provide an improved combustion tube where replacement of component pieces is easily achieved.

It is yet another object of the present invention to provide an improved combustion tube where catalytic material is preserved throughout the combustion process.

In satisfaction of these and other related objectives, Applicant's present invention provides an improved combustion tube characterized by bifurcated inert and catalyst chambers. That is, an inert (energy absorbing) material of the tube is decoupled from the catalyst material. Further, the novel design of the present invention decreases the amount of catalyst utilized and greatly increases the working efficiency of the overall combustion system. Gas flow within the improved combustion tube is of a general "U-shape." This design allows for uniform thermal gradients within the flow and promotes the deposit of unwanted matter along the bottom surface of the tube.

In the present device, as in the case of instruments known in the art, upon impact of the sample on the top layer of the quartz chips, quartz beads, or other inert particles (beads, rods, tubes, or crushed pieces of the same), the energy of the liquid being converted to steam, and the corresponding rapid expansion of the resulting gas, is transferred to the very bottom of the reactor tube. This energy transfer occurs both in the gas phase as well as by direct solid-to-solid contact between the quartz chips or beads.

However at this point, a difference in energy transfer is observed. Since the catalyst chamber, and the catalyst material contained therein, are no longer in direct contact with the energy absorbing layer of quartz (or other inert material), energy transfer by direct contact between particles does not occur. As such, the pressure pulse is severely attenuated by the quartz particles and the resulting gas expansion energy (due to physically increasing the flow rate through the reactor tube) does not result in significant chipping or flaking of the platinum catalyst.

An alternative embodiment of the present invention is characterized by a concentric tube design where an inner tube lies within an outer catalyst tube. In this design, the sample is injected in the inner inlet chamber. The inlet chamber is packed as described above, with quartz chips, beads, or other inert materials. The packing in the inlet serves (as described above) to absorb the thermal shock and dissipate the energy without the direct particle to particle transfer of this energy to the catalyst. The catalyst is located in the space between the outer wall of the catalyst tube and the outer wall of the inert tube. An aperture that allows air flow is located at the base of the combustion tube. This feature allows inert particles to lodge along the bottom surface of the combustion tube without blocking gas flow through the tube. This mechanism virtually eliminates the contamination of the catalytic surface.

Because of the bifurcated chamber configuration, the catalyst chamber is located in a region of maximum thermal stability, i.e. next to the furnace wall. Although the inner tube "cools" due to the heat of vaporization of the aqueous sample, the catalyst itself remains at constant temperature. This feature is extremely beneficial as the temperature at which the sample is vaporized is not a critical parameter; however, the temperature of the catalyst for ensuring complete oxidative combustion is critical. Moreover, thermal energy will not transfer to the center tube by conduction until after the oxidative combustion of the sample has been completed.

After a sufficient number of samples have been injected, the build-up of inorganic salts and/or oxides can eventually begin to plug the inlet chamber. However, since the inlet chamber consists of a simple tube, removal of the tube, packing material, and inorganic salts and/or oxides that have been deposited in the inlet tube are easily replaced with another tube containing the inert packing material. The inexpensive quartz chips can be readily replaced while the catalyst can be reinstalled without any additional conditioning or user preparation required. The reuse of the catalyst is of economic importance to the user.

BRIEF DESCRIPTION OF THE DRAWINGS

Applicant's invention may be further understood from a description of the accompanying drawings, wherein unless otherwise specified, like referenced numerals are intended to depict like components in the various views.

DETAILED DESCRIPTION OF THE PREFERRED EMBODIMENT

Figure 1:
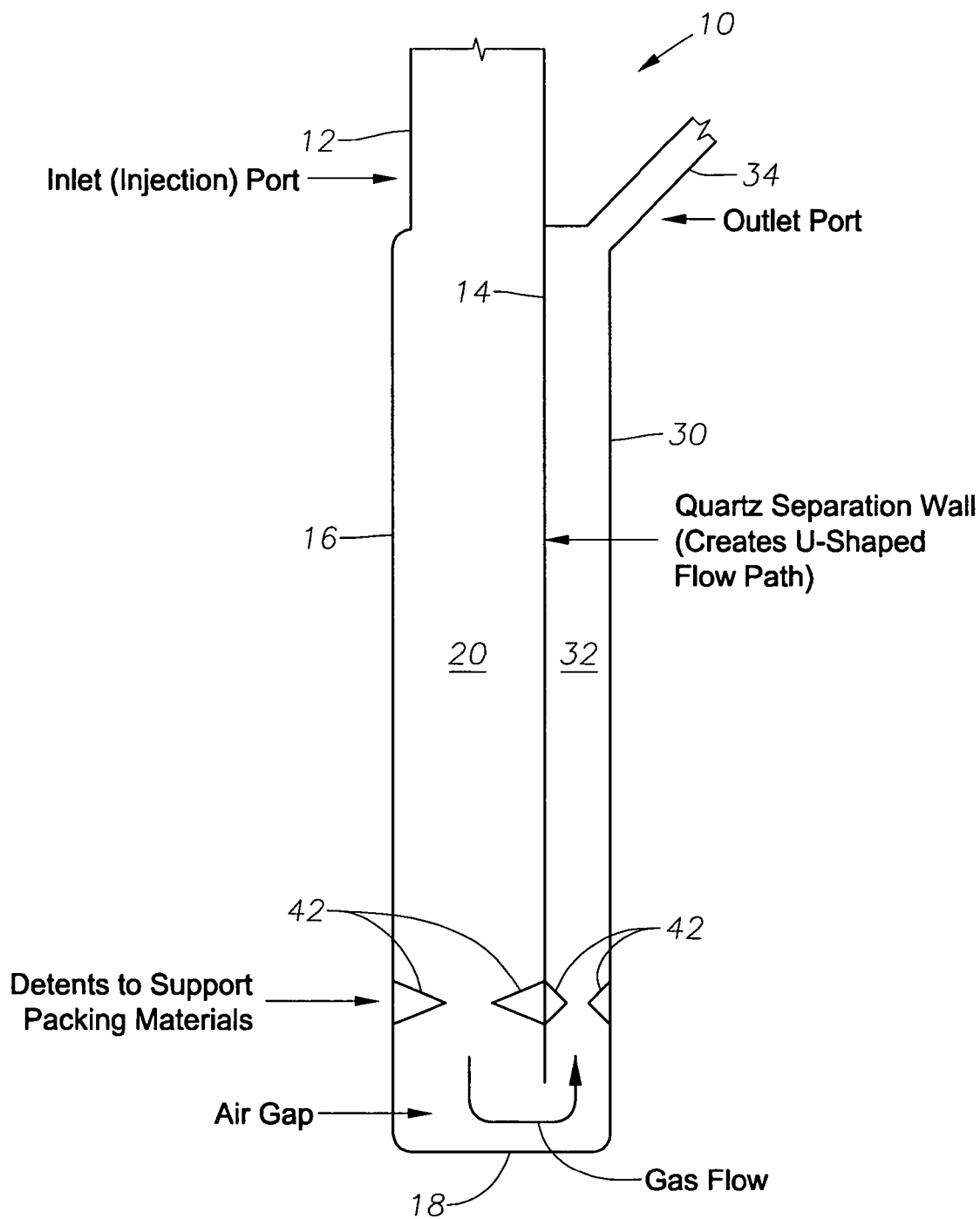
FIG. 1 is a cross sectional view of the preferred embodiment of the improved combustion tube of the present invention.

Referring to FIG. 1, the preferred embodiment of the apparatus of the present invention is generally designated by numeral 10. In the preferred embodiment, apparatus 10 is primarily composed of an inert, non-catalytic material, such as quartz. However, other suitable materials having sufficient characteristics will be apparent to those skilled in the art.

Apparatus 10 is characterized by inlet port 12, whereby an analyte sample is inserted or injected into apparatus 10. Injection port 12 is primarily defined by first outer surface 16 and separation wall 14. In the preferred embodiment, an analyte sample may be injected into apparatus 10 by automated or manual means, as known in the art. As such, injection port 12 may be configured in such a manner so as to allow for proper injection by any such means known in the art.

As best seen in FIG. 1, inert chamber 20 is defined as first outer surface 16 and separation wall 14 extend, in adjacent fashion, from injection port 12 toward bottom surface 18. That is, inert chamber 20 lies below injection port 12 and above bottom surface 18, demarcated by first outer surface 16 and separation wall 14. Inert chamber 20, in the preferred embodiment, contains inert materials 40.

Figure 2:
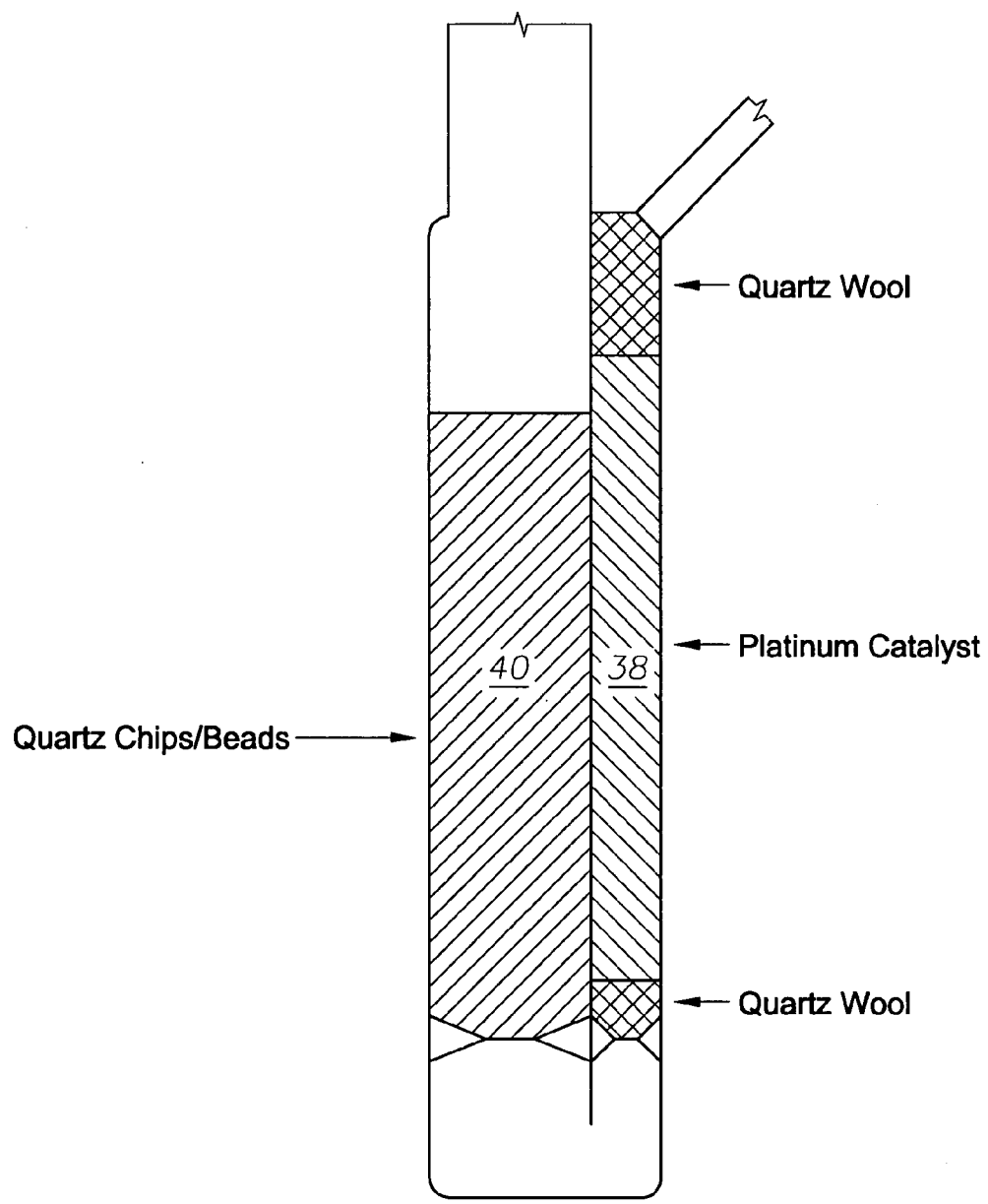
FIG. 2 is a cross sectional view of the preferred embodiment of the improved combustion tube of the present invention, wherein its inner constituents are further depicted.

Referring now to FIG. 2, inert material 40 is positioned within inert chamber 20. In the preferred embodiment, inert material 40 primarily consists of material such as quartz beads or quartz chips. As previously discussed, these materials are meant to bear the brunt of the induced shock from the sample vaporization (expansion) as it enters the combustion tube. Again, as these materials absorb the shock wave energy, some degradation is unavoidable. However, apparatus 10, through incorporation of separation wall 14, and other novel attributes to be fully discussed, eliminates the problems previously associated with such degradation.

Specifically, the unique configuration of device 10 allows broken/chipped material to fall onto bottom surface 18 without obstructing gas flow to catalytic chamber 32 of apparatus 10. Also, the dual-chamber nature of apparatus 10 prevents the inert materials of inert chamber 20 from contacting with the catalytic materials of catalytic chamber 32.

Apparatus 10, in the preferred embodiment, is further characterized by outlet port 34, whereby an analyte sample egresses from apparatus 10. Outlet port 34 is primarily defined by second outer surface 30 and separation wall 14. In the preferred embodiment, outlet port 34 is typically at temperatures below 200 C, and may be configured to allow conventional coupling of the reactor tube to Teflon or other inert tubing for transport to a bulk water condenser element and/or high efficiency drying element. A high efficiency drying element may be chemical or be composed of a single or several 'nation' type driers. The initial nafion drier being heated to temperatures above 100 C (nominally between 150 and 120 C), and the secondary nafion drier being held at or near room temperature. Such devices are available from PermaPure, as either single (initial drier heated, and is then coupled to a second device which is not heated, or coupled (contains both the heated and non heated regions on a single device) element.

In addition, as second outer surface 30 and separation wall 14 extend, in adjacent fashion, from outlet port 34 towards bottoms surface 18, catalytic chamber 32 is defined. That is, catalytic chamber 32 lies below outlet port 34 and above bottom surface 18, demarcated by second outer surface 30 and separation wall 14.

Referring again to FIG. 2, catalytic chamber 32, in the preferred embodiment, contains catalytically active materials 38. In the preferred embodiment, catalytically active materials 38 are generally materials such as platinum on an alumina, zirconia, or titania substrate. As previously discussed, catalytic materials 38 are primarily responsible for the high efficiency of the oxidative process. By virtue of novel configuration of apparatus 10 the integrity of catalytic materials 38 is maintained. Also, such configuration provides for constant catalyst temperature. As such, apparatus 10 is more effective, requires less maintenance, and provides for easier component material replacement in view of the prior art. Further, this design facilitates easy service and removal of inert materials as the tube need only be opened from the injection port 32. Importantly, during this process catalytically active materials 38 are left undisturbed. This is simply not possible with prior art devices.

A plurality of detents 42 rest just above bottom surface 18 and are positioned along each respective chamber. Detents 42 are attached within both inert chamber 20 and catalytic chamber 32, and are configured so that each detent 42 extends toward the other. The resulting arrangement formed by the combination of detents 42 is a "bottleneck" within each chamber. Detents 42 aid in the support of inert material 40 and catalytic material 38, and help hold the respective materials fixed with respect to one another.

As best seen in FIG. 1, separation wall 14 extends, along the interior defined by the combination of first outer surface 16, bottom surface 18, and second outer surface 30. However, separation wall 14 does not span the entire length of the interior, so that an aperture exists between separation wall 14 and bottom surface 18. The interior shape defined by the combination of first outer surface 16, bottom surface 18, second outer surface 30, and separation wall 14 causes a "U-shaped" flow path for the sample as it traverses through apparatus 10. Specifically, an analyte enters through injection port 12, is pushed through inert chamber 20, toward bottom surface 18, and around separation wall 14, up through catalyst chamber 32 and out through outlet port 34.

Figure 3:
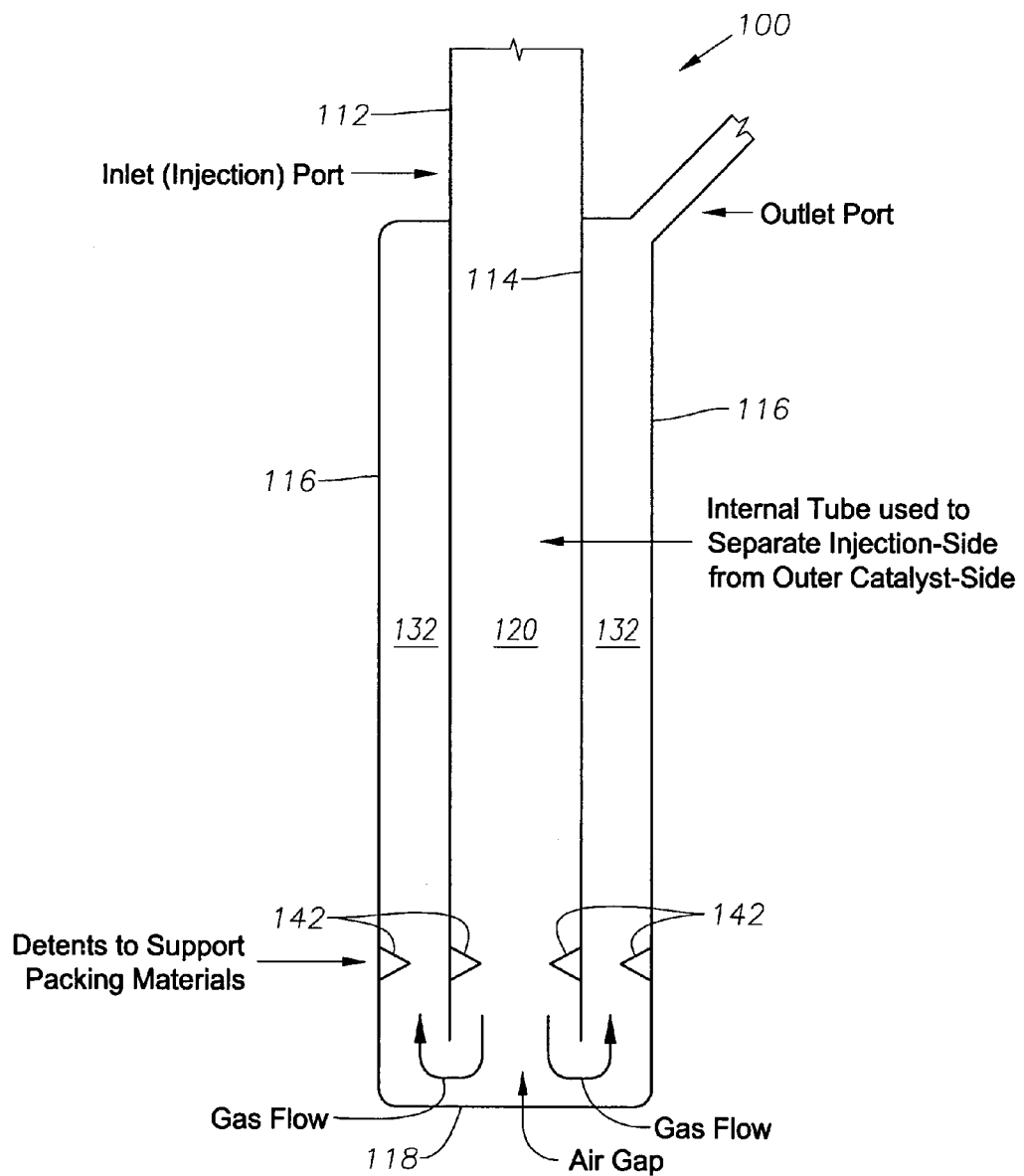
FIG. 3 is a cross sectional view of an alternative embodiment of the improved combustion tube of the present invention.

Referring to FIG. 3, an alternative embodiment of the present invention is generally designated by the numeral 100. In this alternative embodiment, apparatus 100 is primarily distinguished by an inner cylinder lying within an outer cylinder, rather than distinct chambers being partition by a separation wall as in the preferred embodiment.

Apparatus 100 is characterized by inlet port 112, whereby an analyte sample is inserted or injected into apparatus 100. Injection port 112 is primarily defined by inner cylinder wall 114. In the preferred embodiment, an analyte sample may be injected into apparatus 100 by automated or manual means, as known in the art. As such, injection port 112 may be configured in such a manner so as to allow for proper injection by any such means known in the art.

As best seen in FIG. 3, as inner cylinder surface 114 extends toward bottom surface 118, inert chamber 120 is defined. That is, inert chamber 120 lies below injection port 112 and above bottom surface 118, demarcated within inner cylinder surface 114. Inert chamber 120, in this embodiment, contains inert materials 140.

Figure 4:
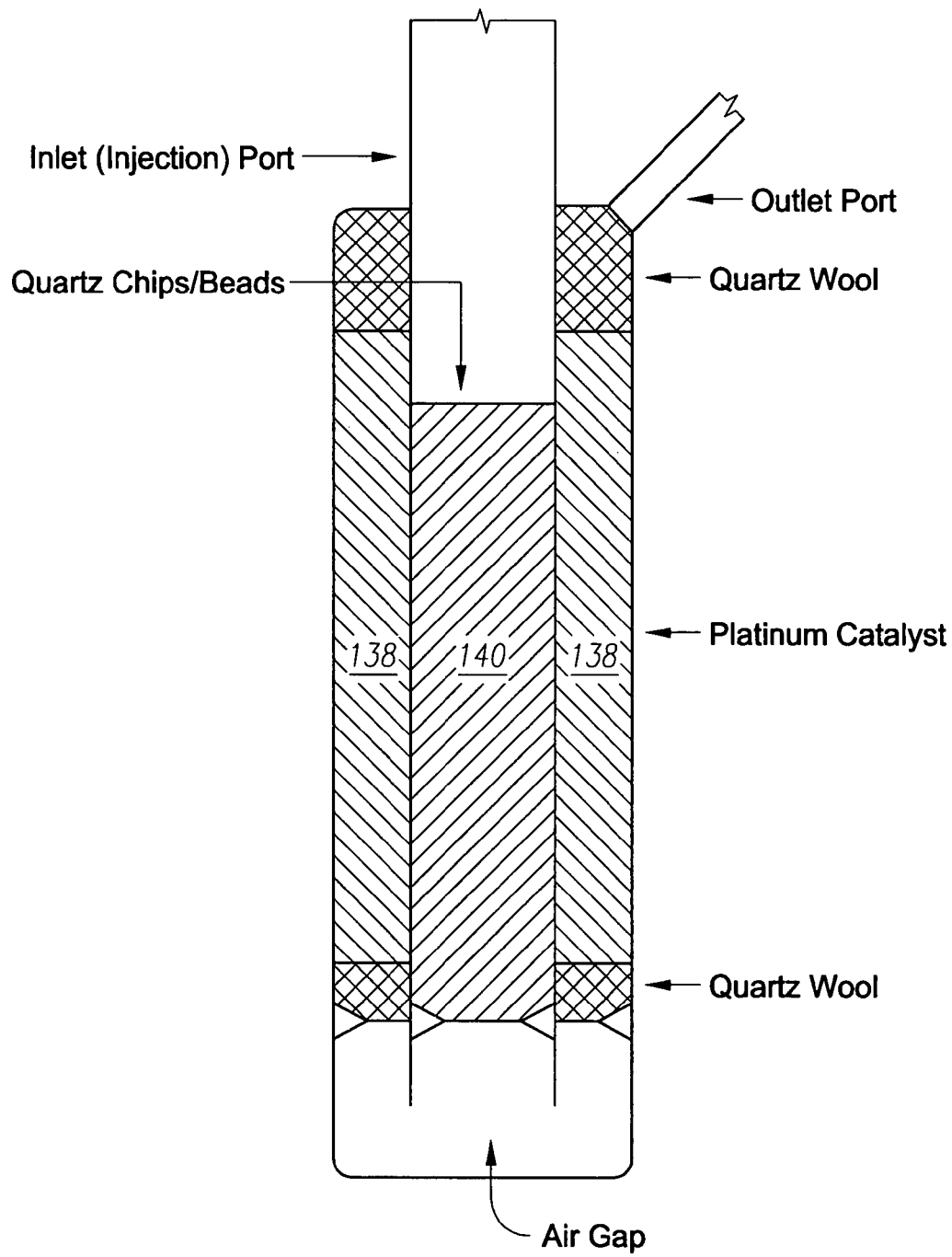
FIG. 4 is a cross sectional view of an alternative embodiment of the improved combustion tube of the present invention, wherein its inner constituents are further depicted.

Referring now to FIG. 4, inert material 140 is positioned within inert chamber 120. In this embodiment, inert material 140 primarily consists of material such as quartz beads or quartz chips. As previously discussed, these materials are meant to bear the brunt of the induced shock wave from the sample vaporization process as it enters the combustion tube. Again, as these materials absorb the shock wave energy, some degradation is unavoidable. However, apparatus 100, through incorporation of inner cylinder surface 114, and other novel attributes to be fully discussed, eliminates the problems previously associated with such degradation.

Specifically, the unique configuration of device 100 allows broken/chipped material to fall onto bottom surface 118 without obstructing gas flow to catalytic chamber 132 of apparatus 100. Also, the dual-chamber nature of apparatus 100 prevents inert material 140 of inert chamber 120 from contacting with the catalytic material 138 of catalytic chamber 132.

Apparatus 100, in this embodiment, is further characterized by outlet port 134, whereby an analyte sample egresses from apparatus 100. Outlet port 134 extends as an aperture from outer cylinder surface 116. In the preferred embodiment, outlet port 134 is typically at temperatures below 200 C, and may be configured to allow conventional coupling of the reactor tube to Teflon or other inert tubing for transport to a bulk water condenser element and/or high efficiency drying element (as described above).

In addition, as outer cylinder surface 116 and inner cylinder surface 114 extend, in adjacent fashion, towards bottoms surface 118, catalytic chamber 132 is defined. That is, catalytic chamber 132 lies below outlet port 134 and above bottom surface 118, bound within second outer cylinder 116 and outside of cylinder surface 114.

Referring again to FIG. 4, catalytic chamber 132, in the preferred embodiment, contains catalytically active materials 138. In this embodiment, catalytically active materials 138 are generally materials such as platinum on an alumina, zirconia, or titania substrate, or platinum as a solid or porous pellet. As previously discussed, catalytic materials 138 are responsible for the oxidative process. By virtue of novel configuration of apparatus 100 the integrity of catalytic materials 138 is maintained. As such, apparatus 100 is more effective, requires less maintenance, and provides for easier component material replacement in view of the prior art.

A plurality of detents 142 rest just above bottom surface 118 and are positioned along each respective chamber. Detents 142 are attached within both inert chamber 120 and catalytic chamber 132, and are configured so that each detent extends toward the other. The resulting arrangement formed by the combination of detents 142 is a "bottleneck" within each chamber. Detents 142 aid in the support inert material 140 or catalytic material 38, and help hold the materials fixed with respect to one another.

As best seen in FIG. 4, inner cylinder 114 extends, in adjacent fashion, along the interior defined by outer cylinder 116, towards bottom surface 118. However, inner cylinder 114 does not span the entire length of the interior, so that an aperture lies between inner cylinder 114 and bottom surface 18. The interior shape defined by the combination of outer cylinder 116, interior cylinder 114, and bottom surface 118, causes a "semi-circular" flow path for the sample as it traverses through apparatus 10. Specifically, an analyte enters through injection port 112, is pushed through inert chamber 120, towards bottom surface 118, and around inner cylinder 114, up through catalyst chamber 132 and out through outlet port 134.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims will cover such modifications that fall within the scope of the invention.

We claim:

1. An apparatus for conducting combustion testing, comprising:
   an elongate reaction tube including a primary segment of substantially U-shaped configuration, said primary segment having a first leg segment, a second leg segment, and a transitional segment intervening said first leg segment and said second leg segment, the respective orientation of said first leg segment, said second leg segment, and said transitional segment forming said substantially U-shaped configuration of said primary segment;
   a first end of said primary segment being configured as an inlet for receiving a sample and a second end of said primary segment being configured as an outlet for sample egress;
   a first length of said first leg segment being configured as an inert chamber containing one or more inert materials and configured for passage of said sample therethrough; and
   a second length of said second leg segment being configured as a catalytic chamber containing one or more catalytic materials and configured for allowing passage of said sample therethrough.

2. The apparatus of claim 1, further comprising:
   a decoupling mechanism configured to isolate said inert material and said catalytic material.

3. The apparatus of claim 1, further comprising:
   a plurality of detents positioned to maintain said inert material within said inert chamber and said catalytic material within said catalytic chamber.

* * * * *